(12) United States Patent
Brondum et al.

(10) Patent No.: US 11,953,459 B2
(45) Date of Patent: Apr. 9, 2024

(54) MULTI-FUNCTIONAL WATER QUALITY SENSOR

(71) Applicants: MASCO CORPORATION, Taylor, MI (US); The Regents of the University of Michigan, Ann Arbor, MI (US)

(72) Inventors: Klaus Brondum, Ann Arbor, MI (US); Mark Andrew Burns, Ann Arbor, MI (US); Wen-Chi Lin, Saline, MI (US); Michael McCague, Escondido, CA (US); Stephen Michael Stec, Dearborn, MI (US); Brian N. Johnson, Ypsilanti, MI (US); Garry Marty, Fishers, IN (US)

(73) Assignees: MASCO CORPORATION, Taylor, MI (US); The Regents of the University of Michigan, Ann Arbor, MI (US)

( * ) Notice: Subject to any disclaimer, the term of this patent is extended or adjusted under 35 U.S.C. 154(b) by 595 days.

(21) Appl. No.: 17/156,255

(22) Filed: Jan. 22, 2021

(65) Prior Publication Data
US 2021/0140904 A1    May 13, 2021

Related U.S. Application Data

(63) Continuation of application No. 14/934,499, filed on Nov. 6, 2015, now Pat. No. 10,900,921.
(Continued)

(51) Int. Cl.
*G01N 27/07* (2006.01)
*G01N 27/30* (2006.01)
(Continued)

(52) U.S. Cl.
CPC ......... *G01N 27/07* (2013.01); *G01N 27/4166* (2013.01); *G01N 33/18* (2013.01); *G01N 27/302* (2013.01)

(58) Field of Classification Search
CPC ..... G01N 33/18; G01N 33/0031; G01N 21/05
See application file for complete search history.

(56) References Cited

U.S. PATENT DOCUMENTS

| 6,255,117 | B1 | 7/2001 | Johnson |
| 6,894,270 | B2 | 5/2005 | Bailey |

(Continued)

FOREIGN PATENT DOCUMENTS

CN    205910610 U    1/2017

OTHER PUBLICATIONS

Extended European Search Report in European Patent Application No. 18182253.7, dated Dec. 11, 2018, 10 pages.
(Continued)

*Primary Examiner* — Jermele M Hollington
*Assistant Examiner* — Temilade S Rhodes-Vivour
(74) *Attorney, Agent, or Firm* — Lempia Summerfield Katz LLC

(57) ABSTRACT

A multi-functional sensor assembly includes an electrically non-conductive substrate defining at least a distal region, intermediary region, and proximal region that are each covered with electrically conductive traces. The proximal region is configured to be exposed to a media to be sensed and the distal and intermediary regions are configured to be protected from the media. The electrically conductive traces comprise at least electrical circuits to sense temperature and flow of the media and one or more electrodes to sense one or more of conductivity, oxidation reduction potential (ORP), and acidity (pH) of the media.

6 Claims, 11 Drawing Sheets

Related U.S. Application Data

(60) Provisional application No. 62/105,237, filed on Jan. 20, 2015.

(51) Int. Cl.
  *G01N 27/416* (2006.01)
  *G01N 33/18* (2006.01)

(56) References Cited

U.S. PATENT DOCUMENTS

| | | |
|---|---|---|
| 7,189,314 B1 | 3/2007 | Pace |
| 7,516,939 B2 | 4/2009 | Bailey |
| 7,581,437 B2 | 9/2009 | Colby |
| 8,987,000 B2 | 3/2015 | Evtodienko |
| 8,993,337 B2 | 3/2015 | Evtodienko |
| 2003/0136960 A1* | 7/2003 | Goodman .......... G01N 33/0031 257/40 |
| 2003/0147777 A1 | 8/2003 | Ghanekar |
| 2003/0198428 A1 | 10/2003 | Humpston |
| 2004/0104130 A1 | 6/2004 | Mosley |
| 2005/0247114 A1* | 11/2005 | Kahn .................. G01N 33/18 73/53.01 |
| 2005/0252790 A1 | 11/2005 | Dobson |
| 2007/0125663 A1 | 6/2007 | Sasanuma |
| 2008/0109175 A1* | 5/2008 | Michalak ................ E03B 7/02 702/50 |
| 2008/0121045 A1* | 5/2008 | Cole .................... G01N 27/226 73/861.08 |
| 2008/0148842 A1 | 6/2008 | Oda |
| 2008/0258742 A1 | 10/2008 | Dimitrakopoulos |
| 2008/0295897 A1 | 12/2008 | Vincent |
| 2009/0282627 A1 | 11/2009 | Porat |
| 2011/0107832 A1 | 5/2011 | Sakuma |
| 2012/0216605 A1 | 8/2012 | Silveri |
| 2013/0145840 A1 | 6/2013 | Asano |
| 2014/0083865 A1 | 3/2014 | Rowhani |
| 2014/0212336 A1 | 7/2014 | Kido |
| 2014/0260566 A1* | 9/2014 | Kahaian ............. G01N 29/2443 73/61.62 |
| 2014/0295569 A1 | 10/2014 | Evtodienko |
| 2014/0299471 A1 | 10/2014 | Mosley |
| 2015/0177042 A1 | 6/2015 | Song |
| 2016/0054249 A1 | 2/2016 | Rateick |
| 2016/0209346 A1 | 7/2016 | Brondum |
| 2016/0232421 A1 | 8/2016 | Decker |
| 2016/0299096 A1 | 10/2016 | Greenwood |

OTHER PUBLICATIONS

Jang et al., "State-of-the-art lab chip sensors for environmental water monitoring", Measurement Science and Technology: 22, Jan. 24, 2011, 18 pages.

Lin et al., "Multifunctional Water Sensors for pH, ORP, and Conductivity Using Only Microfabricated Platinum Electrodes", Sensors, Jul. 19, 2017, 9 pages.

Pellegrino et al., "Robust Multi-Parameter Sensing Probe for Water Monitoring Based on ALD-Coated Metallic Micro-Patterns and Carbon Nanotube Printing", IEEE NEMS 2016—The 11th Annual IEEE International Conference on Nano/Micro Engineered and Molecular Systems, 2016, 2 pages.

* cited by examiner

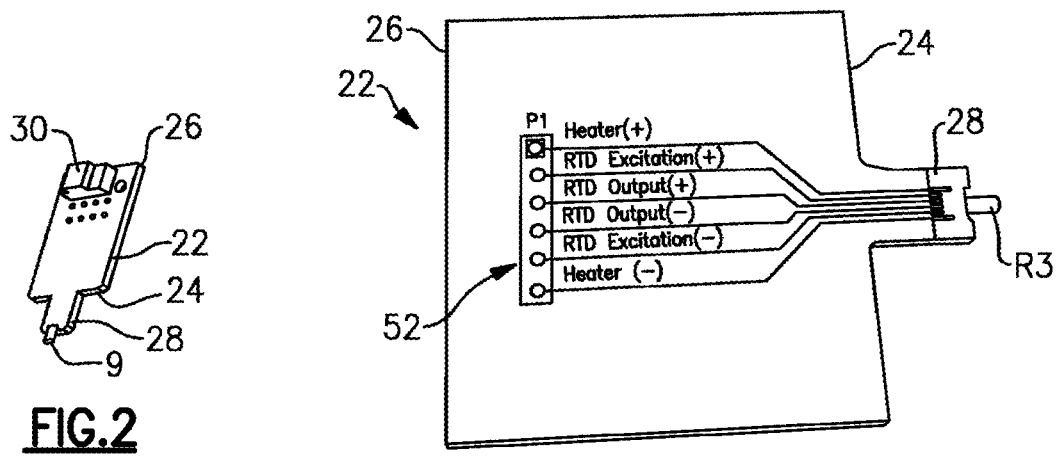
FIG.2
FIG.3
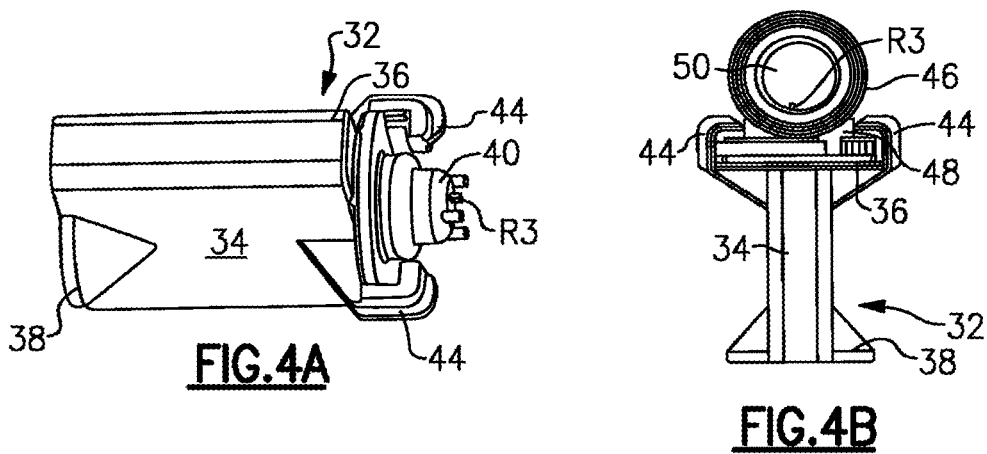
FIG.4A
FIG.4B
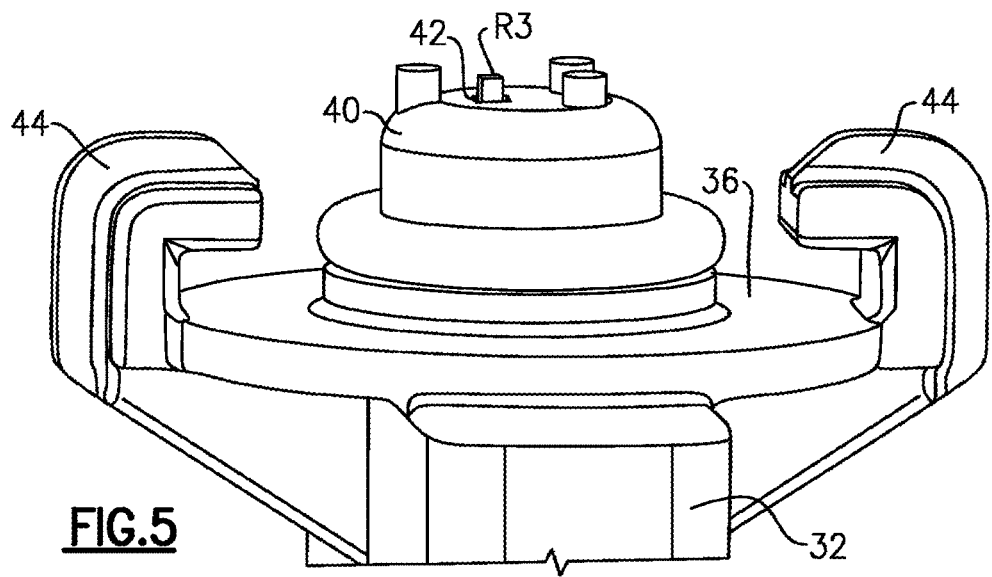
FIG.5

MULTI-FUNCTIONAL WATER QUALITY SENSOR

CROSS-REFERENCES TO RELATED APPLICATIONS

This application is a continuation of U.S. non-provisional application entitled "Multi-Functional Water Quality Sensor," filed Nov. 6, 2015, and assigned Ser. No. 14/934,499, which claimed the benefit of U.S. provisional application filed Jan. 20, 2015, and assigned Ser. No. 62/105,237, the entire disclosures of which are hereby expressly incorporated by reference.

BACKGROUND

The present invention generally relates to a multi-functional flow sensor that is more efficient and cost effective than prior sensor configurations.

One example of a commercial application for this type of sensor is a spa. Typical sensors for monitoring water quality in a spa include in-line sensors, which monitor physical parameters, temperature and flow, and chemical sensors, which monitor conductivity, Oxidation Reduction Potential (ORP) and acidity (pH). These sensors provide information that is used to maintain healthy and safe spa water.

Temperature sensors traditionally used within the industry are of Resistive Temperature Detector (RTD) type, and are typically configured with a stainless steel dome to prevent malfunction due to corrosion and water ingress issues. The protective dome represents a considerable thermal mass that translates into slow response time of the sensor. The temperature sensor has several uses in spa operation, e.g. to determine the temperature of the spa for safety and comfort purposes, to determine temperature correction basis for conductivity measurement, and to provide overheat protection of a water heater for safety purposes. As such, there is a need to provide a temperature sensor with a short response time for the safe operation of the water heater.

Flow sensors for water use are based on a diverse range of concepts including anemometer and impeller types, for example. The impeller type is vulnerable to debris and corrosion, which can block spin wheel rotation and create false low readings. The anemometer type relies on a measurement of difference in resistance of two wires immersed in water, with one the wires being heated. Drift can be caused by precipitation on the heated wire and general elevated corrosion of metal wire. In addition, the anemometer is prone to malfunction when operated out of water or in "no flow" conditions. In some configurations, the anemometer will also have high power consumption preventing standalone battery operation. While flow sensors are preferred, both flow and pressure sensors are used in spa operation, as measure of filter conditions, i.e. measure of degree of blockage, and as protection of the water heater against overheat conditions. As such, there is a need to provide an inexpensive flow sensor in continuous operation for the safe operation of heaters and filters.

Conductivity sensors adopted by industry can be as simple as documenting the DC resistance of two water immersed wires operated at an AC frequency. Sometimes conductivity is translated into total dissolved solids (TDS), requiring a temperature correction of conductivity to produce reliable results. The need for conductivity measure is based on the observation that corrosion generally increases with increased conductivity and therefore translates into general corrosion performance of metal components in spa environments. Further, conductivity gives a general understanding of the amount of chemicals that have been added over time, and which have accumulated in the spa. Finally, conductivity serves as a basis for optimal operation of chlorine generator by electrolysis. Thus, there is also a need for inexpensive conductivity sensor for a spa bath operation.

Traditional ORP and pH sensors are based on reference electrodes, such as silver chloride electrodes, which produce a fixed potential against which other measures can be referenced. A common silver reference electrode is an example of an equilibrium reference. Specific problems are recognized in the operation of pH and ORP sensors based on equilibrium references. First, a membrane, which protects the reference electrolyte from dilution, tends to get clogged up over time due to hard spa water, which increases sensor response time. Second, the well-defined electrolyte surrounding the reference electrode tends to mix with the spa water over time, creating a reference electrode drift. In order to resume original reference sensitivity, pH electrodes are stored in a highly acidic solution to maintain fast response times. Further, the the well-defined reference electrolyte, and if possible the membrane, can be changed in an attempt to maintain spa operation that is free of drift.

While ORP and pH sensors based on the equilibrium reference electrode concept can be operated very accurately and reproducibly, it is not uncommon to see drift and response time issues if not maintained on daily basis for laboratory use or weekly basis for consumer use. Further, the sensor maintenance should be done by skilled operator such as a lab technician to avoid expensive electrode damage. As such, traditional ORP and pH sensors are considered high maintenance in continuous operation. Additionally, these temperature, flow, conductivity, ORP, and pH sensors come packaged individually or in combinations excluding one or more of above mentioned metrics, which adds to installation complexities and cost of combining individual sensors.

Thus, there is a need for an inexpensive water quality sensor that includes temperature, flow, conductivity, ORP and pH measures with fast response, little or no maintenance, and a durability that exceeds months in continuous use with minimal drift and calibration issues.

SUMMARY OF THE DISCLOSURE

According to one exemplary embodiment, a multi-functional sensor assembly includes an electrically non-conductive substrate defining at least a distal region, intermediary region, and proximal region that are each covered with electrically conductive traces. The proximal region is configured to be exposed to a media to be sensed and the distal and intermediary regions are configured to be protected from the media. The electrically conductive traces comprise at least electrical circuits to sense temperature and flow of the media and one or more electrodes to sense one or more of conductivity, oxidation reduction potential (ORP), and acidity (pH) of the media.

In another embodiment according to the previous embodiment, the proximal region includes the one or more electrodes, the intermediary region includes the electrical circuits to sense temperature and flow, and the distal region includes electrically conductive trace segments connected to the electrical circuits and to the one or more electrodes, and wherein the trace segments terminate in pads serving as an external electrical connection interface.

In another embodiment according to any of the previous embodiments, the one or more electrodes comprise at least three electrodes configured to sense conductivity, ORP and pH.

In another embodiment according to any of the previous embodiments, the at least three electrodes comprise three concentric circles interrupted for connection to the electrically conductive traces, and wherein a radially outer electrode comprises a counter electrode, a radially inner electrode comprises a working electrode, and a radially intermediary electrode between the counter and working electrodes comprises a reference electrode.

In another embodiment according to any of the previous embodiments, the electrically non-conductive substrate comprises a single piece substrate that is approximately 4.0 mm by 1.0 mm by 0.5 mm or less.

According to another exemplary embodiment, a multifunctional sensor assembly includes an electrically non-conductive substrate defining at least a distal region, intermediary region, and proximal region that are each covered with electrically conductive traces; a printed circuit board connected to the distal region; and a housing enclosing the intermediary and distal region, and surrounding at least one end of the printed circuit board, and wherein the proximal region extends outwardly of the housing to be exposed to a media to be sensed, and wherein the electrically conductive traces comprise at least electrical circuits to sense temperature and flow of the media and one or more electrodes to sense one or more of conductivity, oxidation reduction potential (ORP) and acidity (pH).

In another embodiment according to any of the previous embodiments, the electrical circuits are located in the intermediary region and comprise a heater circuit and a Resistive Temperature Detector (RTD) circuit that is used to determine temperature and flow rate of the media.

In another embodiment according to any of the previous embodiments, the proximal region includes the one or more electrodes, and wherein the one or more electrodes comprises at least three electrodes configured to sense conductivity, ORP and pH.

In another exemplary embodiment, a pulse anemometer mode of operating a flow sensor includes creating a temperature profile comprised of peak and valley temperatures of a substrate exposed to a media via heat pulses defined by a power, a power duration, and a power off duration; and documenting the peak and valley temperatures of the substrate as a measure of flow and velocity of the media.

In another exemplary embodiment, a dynamic mode of operating a three electrode setup for ORP and pH documentation of a media includes establishing a first constant potential or a first constant current between a working electrode and a counter electrode and documenting a first documented potential between the working electrode and a reference electrode as a measure of ORP of a media; establishing a second constant potential or a second constant current between the working electrode and the counter electrode and documenting a second documented potential between the working electrode and the reference electrode; establishing a third constant potential or a third constant current between the working electrode and the counter electrode and documenting a third documented potential between the working electrode and the reference electrode; and determining a difference between the second and third documented potentials between the working and reference electrodes as a measure of a pH of the media.

These and other features of the present invention can be best understood from the following specification and drawings, the following of which is a brief description.

BRIEF DESCRIPTION OF THE DRAWINGS

FIG. 2 is a perspective view of the sensor assembly of FIG. 1 installed on a printed circuit board.

FIG. 3 a top view of the PCB and sensor assembly.

FIG. 4A is a side view of the sensor assembly installed within a housing.

FIG. 4B is an end view of the sensor and housing assembly of FIG. 4 connected to a pipe.

FIG. 5 is an enlarged side view of one end of the sensor and housing assembly.

DETAILED DESCRIPTION

Figure 1:
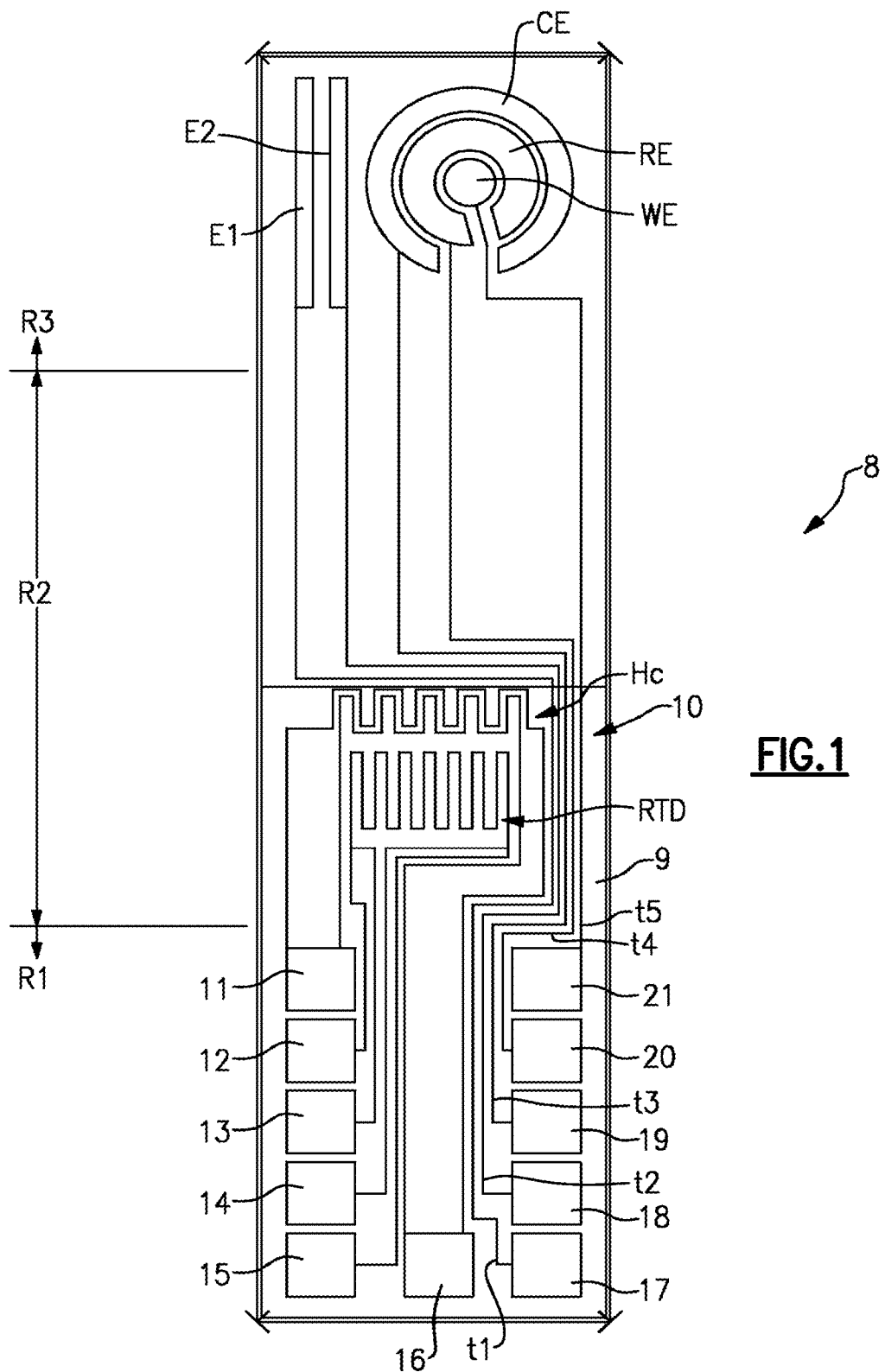
FIG. 1 shows a schematic representation of a multifunctional water quality sensor assembly according to the invention.

FIG. 1 shows a schematic representation of a flow sensor assembly 8 that includes a substrate or chip body 9 and a circuit and sensor assembly 10 supported on the chip body 9 that is configured to determine temperature and flow rate for a liquid, and which is further configured to operate in a plurality of modes to sense a plurality of water conditions. In one example, the plurality of water conditions comprises at least pH (a measure of acidity or basicity of an aqueous solution), ORP (Oxidation Reduction Potential), and chlorine levels. The sensor assembly thus provides lab-on-a-chip (LOAC) capability.

The chip body 9 is significantly smaller than prior configurations and is capable of determining temperature, flow rate, pH, ORP, and chlorine levels in an accurate manner. In one example, the chip body 9 is comprises a single piece substrate that is approximately 4.0 mm by 1.0 mm by 0.5 mm or less. In one example, the substrate or chip body 9 is electrically non-conductive such as, but not restricted to, silicon or glass or an organic polymer such as polyimide, PE or PP or PTFE.

In one example, the chip body 9 is coated using lithographic technology in patterns with a conductive materials such as platinum and titanium and alloys thereof. The resulting sensor assembly 8 has three regions: (1) a first or distal region R1 at a distal end, which serves for external connection; (2) a second region R2, which is an intermediary region and hosts temperature and flow circuitry that are not exposed to a medium to be sensed; and (3) a third region R3 at a proximal end and which hosts electrodes for direct media contact sensing of conductivity, ORP and pH.

The sensor assembly 8 comprises several separate platinum (Pt) circuits, leads, electrodes and pads deposited, in thickness of about 1 μm, on an electrical insulating silicon (Si) substrate as shown in FIG. 1. One circuit $H_C$ acts as resistive heating element and includes segments 11 and 16. Other circuits act as a temperature sensor, referred to as a RTD, and include segments 12, 13, 14 and 15. First and second conductivity electrodes $E_1$, $E_2$ act as a conductivity sensor and include pad segments 17 and 18. Finally, three segments 19, 20 and 21 correspond to the combined ORP and pH sensor electrodes. Pad segment 19 is connected to the pH and ORP sensor counter electrode CE, pad segment 20 is connected to the reference electrode RE, and pad segment 21 is connected to the working electrode WE.

The leads, circuits, electrodes, and bonding pads are laid out in one of the three regions on the chip body 9. The proximal region, or third region R3, holds the pH, ORP and conductivity electrodes CE, RE, WE that are connected to segments 19, 20, 21, and which all are exposed to the medium to be sensed. The intermediary region, or second region R2, holds the temperature and flow circuitries that are entirely overpotted inside a housing. The distal region, or first region R1, holds leads to the intermediary circuits and proximal electrodes through wire bonding pads for external connectivity.

The relatively small size of the sensor assembly 8 is best shown in FIGS. 2-3, which show the chip body 9 mounted to a printed circuit board (PCB) 22. The PCB 22 has a first end 24 and a second end 26. In one example, the chip body 9 is mounted to an extension portion 28 extending outwardly of the first end 24. A connection jack 30 for electrical connections is mounted to the second end 26. The chip body 9 is bonded, e.g. glued, to the, PCB 22 and the chip pads or segments 11-21 are wire bonded to the PCB 22 for preliminary signal conditioning and external connection.

FIG. 3 shows the PCB 22 with the chip body 9 having the third, or proximal, region R3 extending beyond the extension portion 28 of the PCB 22. The chip and board assembly is inserted in a housing 32 (FIGS. 4A-7) that is potted and sealed with resin in order to establish a barrier against media ingress (water) to the first R1 and second R2 regions while exposing region R3 to the flow media. The assembled sensor is interfacing with support electronics for powering, excitation patterns, and sequencing and signal conditioning for sensor output display.

Figure 6:
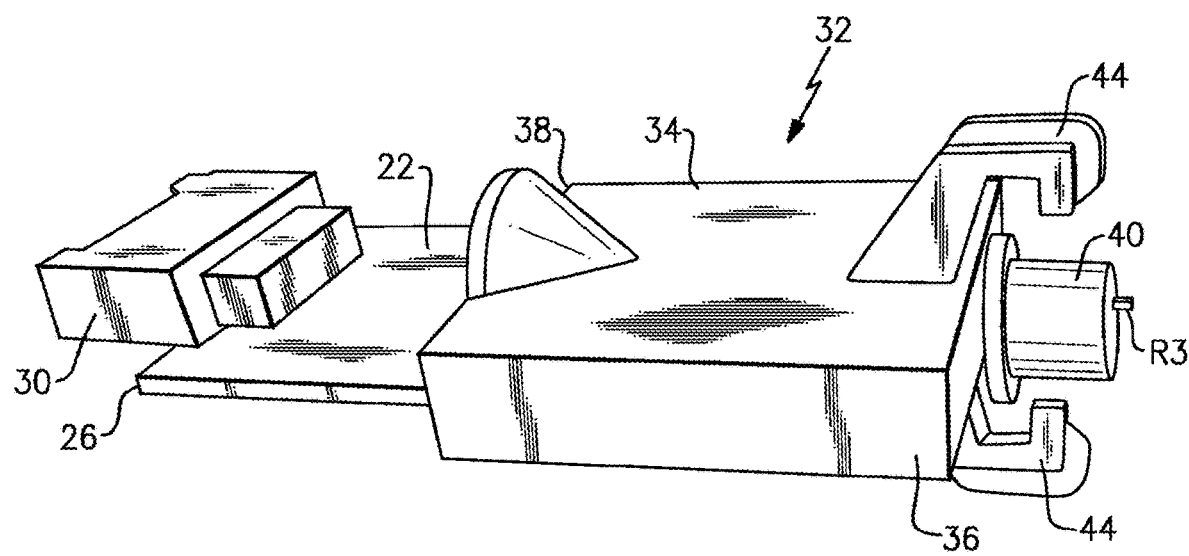
FIG. 6 is a side view of an assembly including the housing, sensor, PCB, and electrical connector.

FIG. 4A shows the housing 32, which comprises a body portion 34 having a first end 36 and a second end 38. The first end 36 includes a reduced diameter portion 40 extending axially outward and which includes an opening 42 (FIG. 5). The third region R3 extends through this opening 42 and axially beyond the reduced diameter portion 40 as shown in FIGS. 4A and 5-6. The reduced diameter portion 40 includes attachment features 44 that couple the housing 32 to a tube 46 through which the medium flows as shown in FIG. 7.

In one example, the attachment features 44 comprise arms that fit around a flange mount 48 formed on the tube 46; however, other attachment structures could also be used. The tube 46 defines an open inner conduit 50 that defines a flow path for the flowing medium. When the housing 32 is coupled to the tube 46, the third region R3 extends into the flow path as shown in FIG. 4B.

Figure 7:
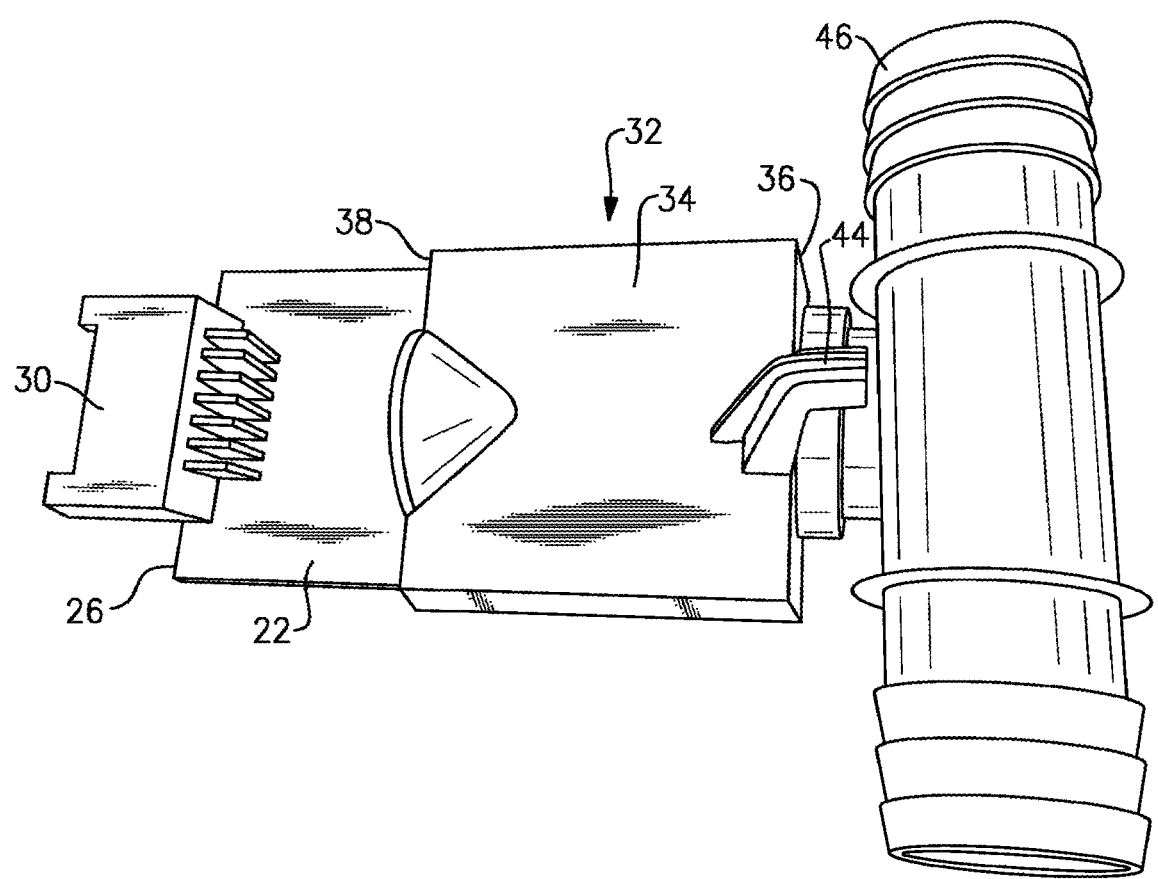
FIG. 7 is a top view of the assembly of FIG. 6 connected to a pipe.

The PCB 22 extends outwardly of the second end 38 of the housing 32 (FIGS. 6-7). The second end 26 of the PCB 22 is thus exposed such that the connection jack 30 can be coupled to a connection interface 52 (FIG. 3) on the PCB 22.

Traces $t_1$, $t_2$ connect pad segments 17, 18 to the conductivity electrodes $E_1$, $E_2$, and traces $t_3$, $t_4$, $t_5$ connect pad segments 19, 20, 21 to the counter electrode CE, reference electrode RE, and working electrode WE. The traces $t_{1-5}$ extend across the intermediary region R2 and into the third region R3. As such, portions of the traces $t_{1-5}$ are exposed to the flowing water. One will realize that the water exposed portion of these traces $t_{1-5}$ differs in area and relative orientation but can be interchanged such that any three electrodes (CE, RE, WE) can be configured for pH, ORP and chlorine sensing while any two electrodes $E_1$, $E_2$, can be configured for conductivity sensing. For the same reason, three electrodes can be configured for all the aforementioned sensing jobs: conductivity, pH, ORP and chlorine separated by mode of operation in time or sequence or overlapping. For example, the conductivity mode of operation is done via documentation of $I_{rms}$ resulting from a 6 kHz, 0.25V signal that for all practical purposes can, by overlaying a DC signal, be used for documenting pH, ORP and chlorine levels. An analogy would be signals carrying radio transmissions where the audible portion of the signal is carried as perturbations of a carrier wavelength such as a signal for a radio station.

The purpose of the invention is to create a multi-functional sensor assembly 8 with combinations of temperature, flow conductivity, pH, ORP, and chlorine sensing capabilities and associated sensor operation modes for general purpose and low cost sensing for commercial plumbing related applications. The sensor assembly 8 utilizes low cost Si chip or glass substrates and utilizes standard processing for high volume manufacturing of microchips in combination with unique mode of control allowing for sensing. This will be discussed in greater detail below.

The temperature is derived from the resistance of the sensor circuitry. The concept of measuring temperature with RTD is well known in the art. However, the subject invention uses a heat pulse technique to determine both temperature and flow using the same single sensor circuit. The flow is derived from the temperature sensor when the heating element 11, 16 is powered. Essentially, the power gives rise to a temperature increase that is dissipated. The heat dissipation is a function of the cooling rate of the chip that is inversely proportional to the flow velocity of fluid passing the sensor. The peak temperature can be translated into a flow.

Several advantages are achieved by operating the heating element in pulsed power loads. First, the overall power needed to operate the flow function is reduced. Second, the chip is protected from overheating in situations where the cooling rate is low, i.e. no flow. Third, a large response is provided in short time span. By reducing the thermal mass of chip, the response time can be reduced to range of seconds and sub-seconds. Finally, temperature measurement is enabled in a "power off mode" and flow is enabled in a "power on mode," and consequently only one temperature sensor is needed for flow and temperature sensing.

By reducing the thermal mass of chip, the response time can be reduced to range of seconds and sub-seconds. A fast response can be achieved by using a substrate with high thermal conductivity properties such as silicon. Similarly the power needed to provoke such response is lowered by using a substrate with high thermal conductivity such as silicon (see examples 1, 2 and 7 below).

Figure 8:
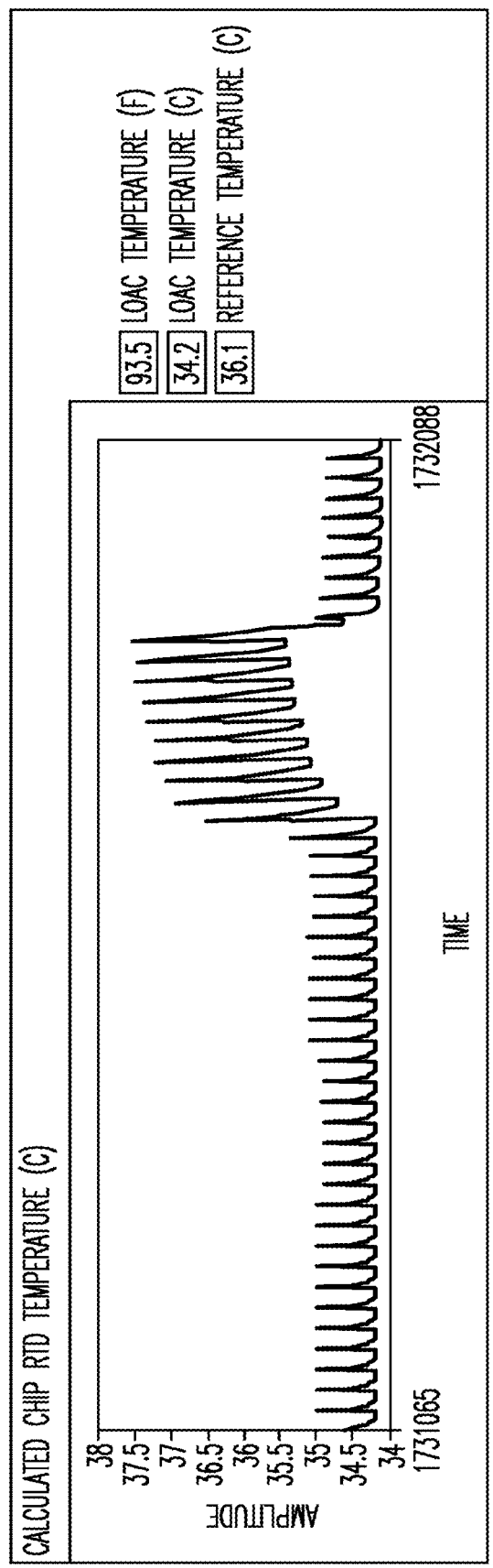
FIG. 8 shows amplitude v. time for a calculated chip RTD temperature.

FIG. 8 shows sensor response during flow excursions. FIG. 8 shows amplitude v. time for a calculated chip RTD temperature and thus shows a LOAC temperature response following a change in flow. FIG. 8 shows the LOAC response in temperature to repeated heat pulses to heater circuit 11, 16 of duration of 200 ms every 1000 ms creating distinct peak temperatures and base or valley temperatures. Peak temperature is inversely related to flow velocity and flow.

Figure 9:
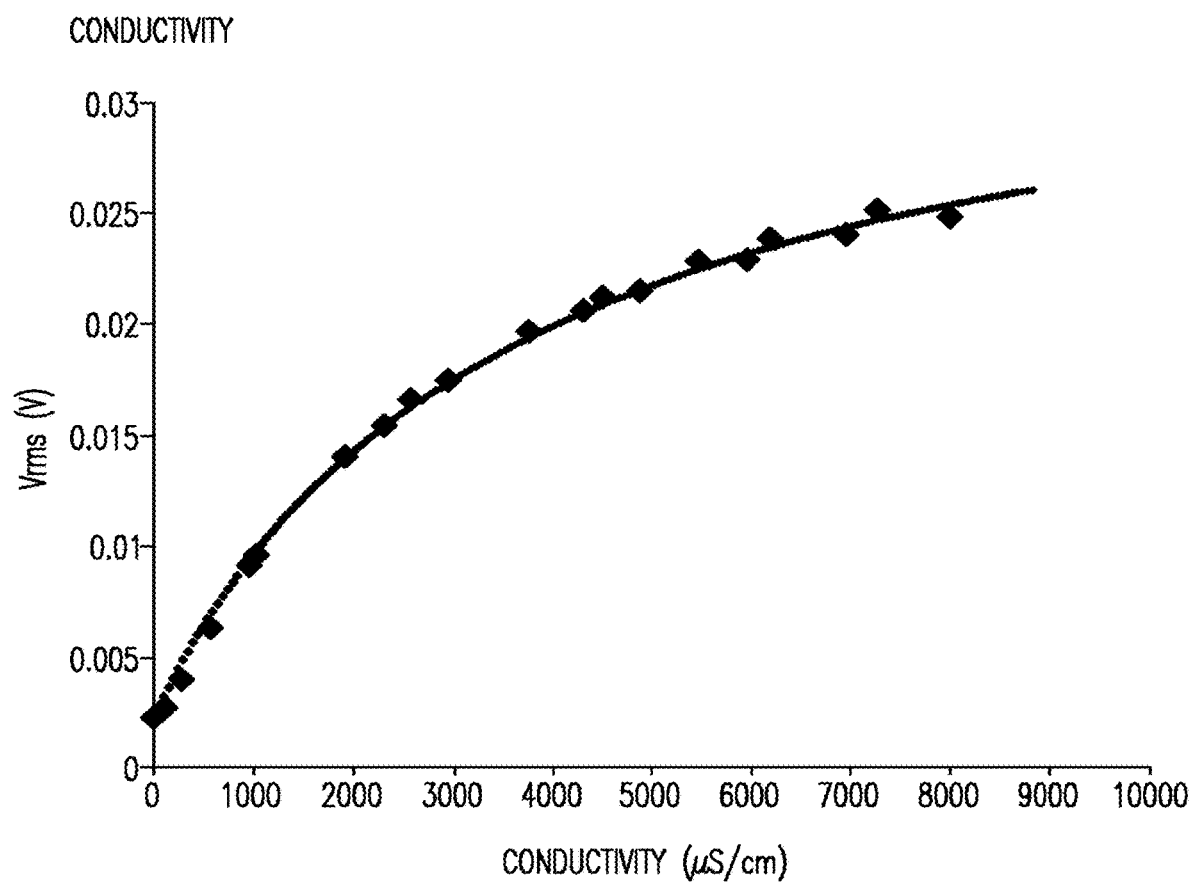
FIG. 9 shows $V_{rms}$ v. Conductivity.

Conductivity sensing is done by documenting the DC resistance of two water immersed wires operated at an AC frequency. Sometimes conductivity is translated into total dissolved solids, requiring a temperature correction of conductivity to produce reliable results. Example 3 below describes how this is done, and FIG. 9 shows the sensor response to exposure to waters of increasing conductivity created by sodium chloride additions. More specifically, FIG. 9 shows $V_{rms}$ v. Conductivity, and depicts LOAC sensor response following a change in conductivity caused by adding sodium chloride to the spa chemistry, displayed along with calibrated reference conductivity measurement.

In one example, the following temperature and flow algorithms were used:

$$T = mV + b$$

This algorithm states that temperature is a linear function of a voltage drop over a resistor given a known current. Sensors based on this temperature sensitive resistor method are broadly referred to as RTD.

$$F_{(T)} = a\left(1 + \left|\frac{dT}{dt}\right|\right)^1 \left(1 + \frac{\Delta T_{cal}}{T_{cal}}\right)^m \Delta T_{pulse}^n + b$$

This algorithm inversely correlates the flow with the temperature increase as documented by sensor induced by a power load to a heater circuit located close to the sensor. Sensors documenting flow through cooling rate are known as anemometers. The complexity of the above algorithm is due to the fact that a voltage pulse is being used, which does not give a constant power with temperature, necessitating the incorporation of correction factors. One of the inventive features is the use of this pulsed power which allows the use of the RTD to document both flow and temperature.

Conventional electrochemical theory on sensors is based on equilibrium type of solutions, i.e. reference electrodes in designed electrolytes separated from medium of interest by high resistivity salt bridge to which a sensor electrode is referred for obtaining absolute values. The sensor electrode may be covered with ion selective membrane for increased sensitivity for specific ions.

The three electrode type of configuration shown in FIG. 1 is adopted for advanced characterization in disciplines like cyclic voltammetry and impedance spectroscopy. FIG. 1 shows the counter electrode CE, reference electrode RE, and working electrode WE connected to pad segments 19, 20 and 21. The equilibrium approach traditionally teaches that when using a silver chloride reference electrode in dedicated electrolyte, polarization is established between the working electrode WE and the reference electrode RE while running current between the working electrode WE and the counter electrode CE thereby generating characteristics for the working electrode WE. In this configuration, monitoring equilibrium potential between the working electrode WE and the reference electrode RE, also called open circuit voltage, OCV, will produce a potential that can be translated into an ORP after correction for the silver chloride reference standard potential. Similarly, covering the working electrode WE with an ion selective film such as Nafion and documenting the OCV between the working electrode WE and the reference electrode RE will produce a potential dominated by proton activity, translatable to pH with appropriate correction for the reference electrode.

These equilibrium approaches are highly effective in creating desired results however they have shortcomings in terms of time, cost and durability.

For example, a significant amount of time is required in order to establish equilibrium in a system operated at high resistance—often several minutes. Also, cost significantly increases when manufacturing physically complicated reference electrodes and highly specialized membranes for sensor electrodes. Further, the durability of the equilibrium approach is limited because reference electrodes are operated in inherently non-equilibrium environments requiring maintenance for sustained operation, and because ion-selective membranes have a tendency to foul up, producing drift and delayed time response.

Using the dynamic sensor approach overcomes these limitations. The dynamic approach determines pH, ORP and chlorine levels using a single dedicated three electrode sensor. As discussed above, FIG. 1 shows the counter electrode CE, reference electrode RE, and working electrode WE connected to pad segments 19, 20 and 21. The approach polarizes (draws current) between the working electrode WE and the counter electrode CE and follows the temporal development in potential between the working electrode WE and the reference electrode RE, which is a response that is ORP and pH dependent.

Figure 10:
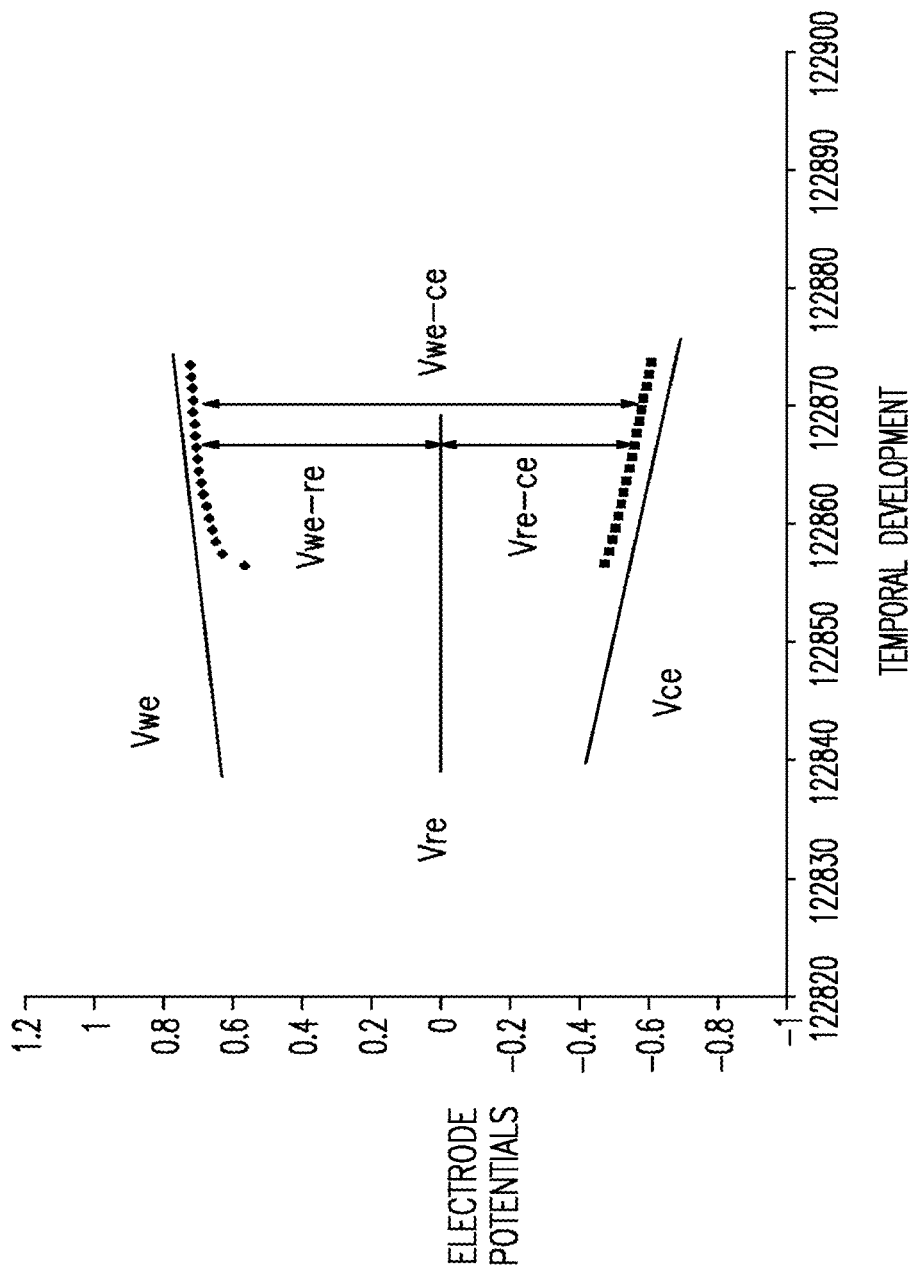
FIG. 10 shows the LOAC sensor response following a polarization event in time.

Polarization between working electrode WE and the counter electrode CE, $V_{WE-CE}$, creates a potential between working electrode WE and reference electrode RE. $V_{WE-CE}$, is dependent on the degree of polarization and the ORP of the solution. Such a polarization is shown in FIG. 10. FIG. 10 shows the LOAC sensor response following a polarization event in time. The graph shows temporal development (horizontal axis) of electrode potentials (vertical scale) derived from running the three electrode sensor at 600 nA between the working electrode WE and the counter electrode CE Pt electrodes with the floating the reference electrode RE. The various potentials $V_{RE}$, $V_{WE-CE}$, $V_{WE-RE}$ and $V_{RE-CE}$ are shown on the graph. The solid lines are introduced to guide the eye.

Figure 11:
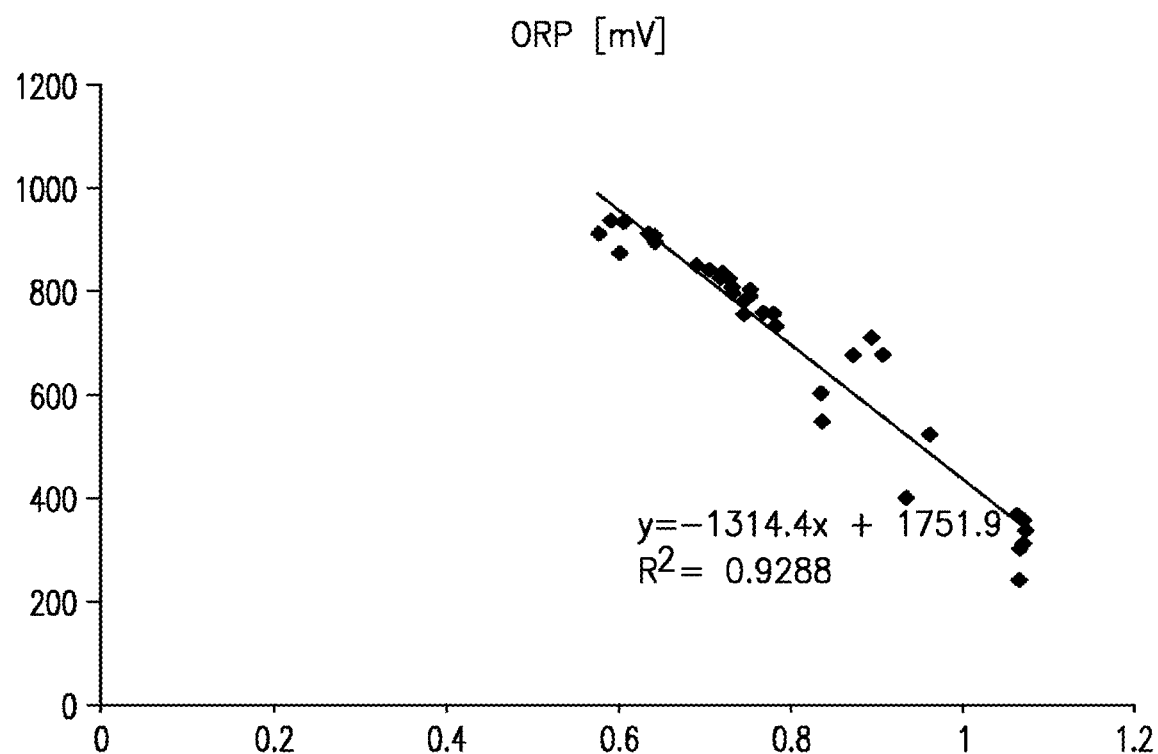
FIG. 11 graph shows LOAC sensor ORP responses following a change in ORP.

Practical experiments have shown that changing the ORP of the solution for any given polarization exceeding approximately 0.7 V is directly correlated to the $V_{EW-ER}$ potential observed between working electrode and reference electrode. Such an ORP relation is shown in FIG. 11 for $V_{WE-RE}$ vs ORP. The FIG. 11 graph shows LOAC sensor ORP responses following a change in ORP caused by adding sodium DiChlororCyanurate (DCCy), sodium chloride, sodium bisulfate, sodium bicarbonate to the spa chemistry—displayed along with calibrated reference ORP measurement. In practice one should not exceed 1.5 V polarization for extended time as hydrogen gas evolution will create time fluctuations in the electrode area and provoke a noisy relation.

Figure 12:
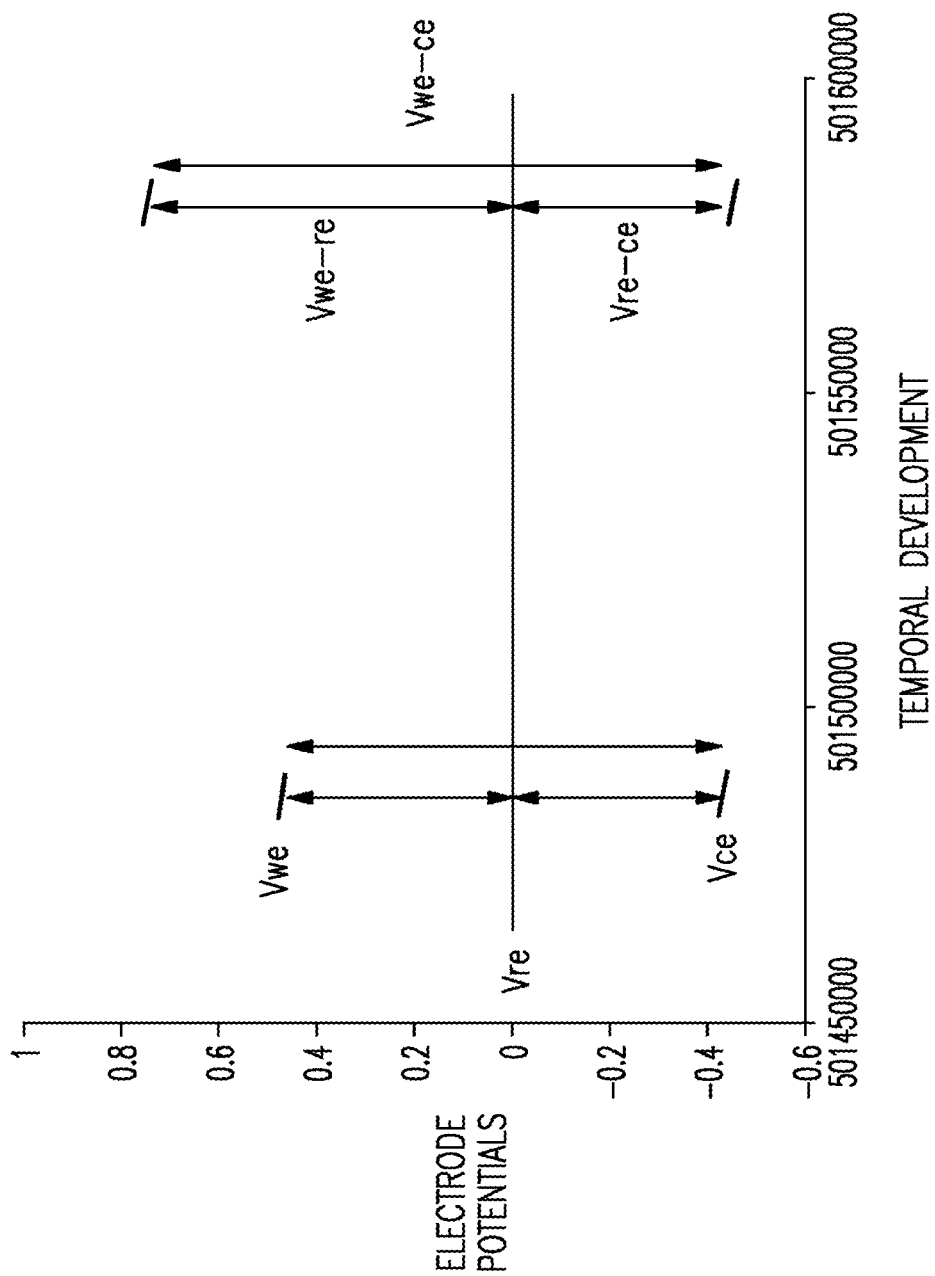
FIG. 12 shows the LOAC sensor response following a polarization event in time.

FIG. 12 shows the LOAC sensor response following a polarization event in time. The graphs shows temporal development (horizontal axis) of electrode potentials (vertical scale) derived from running the three electrode sensor at 0.9 V and 1.2 V between the working WE and the counter CE Pt electrodes with floating the reference electrode RE.

A change in the $V_{WE-CE}$ polarization gives rise to a change in $V_{WE-RE}$. Practical experiments have shown that, focusing on the interval of 0.7 V-1.5 V for $V_{WE-CE}$ potential, a change of 0.3 V, $V_{WE-CE}$, from approximately 0.9 V to 1.2 V gives rise to a change in □ $V_{WE-RE}$ that correlates with pH. FIGS.

13 and 14 show □ $V_{WE-RE}$ vs pH for correlations in chloride high solution and chloride low solution.

Figure 13:
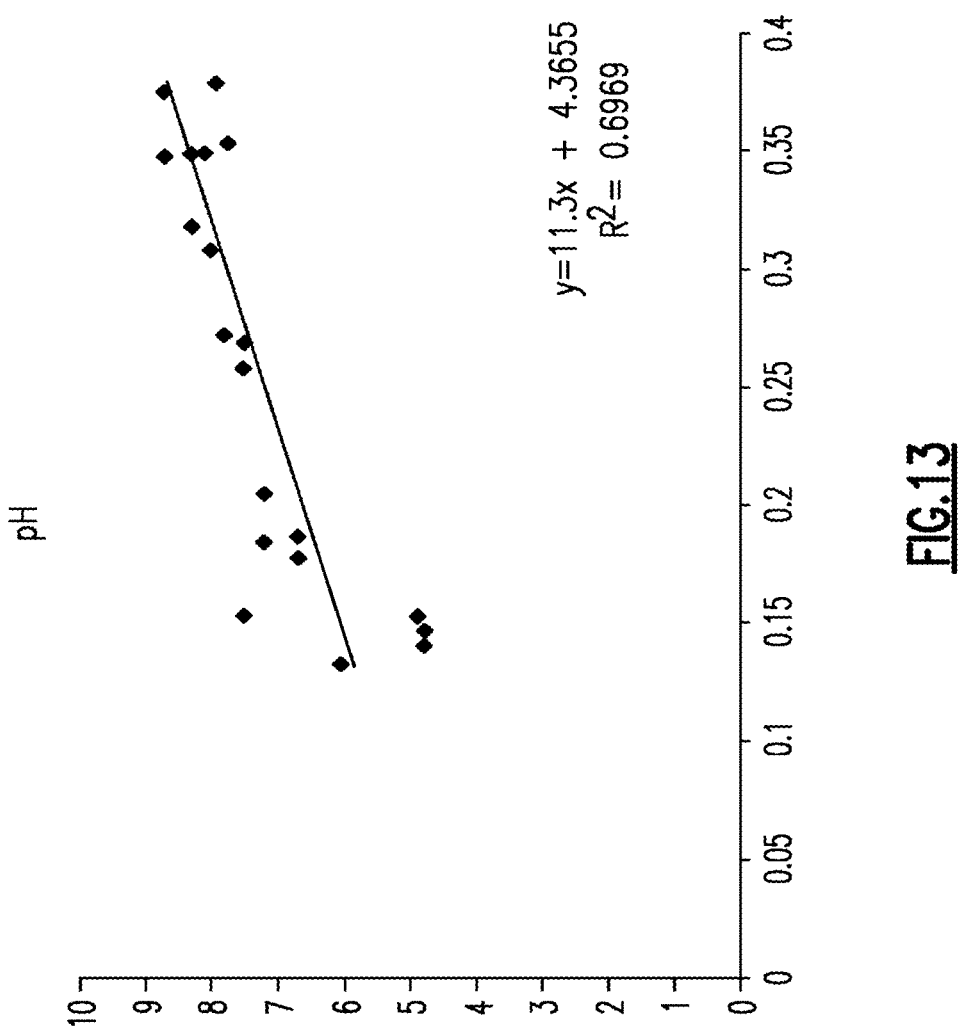
FIG. 13 shows pH vs $\Delta V_{WE-RE}$ for a high chloride result.
Figure 14:
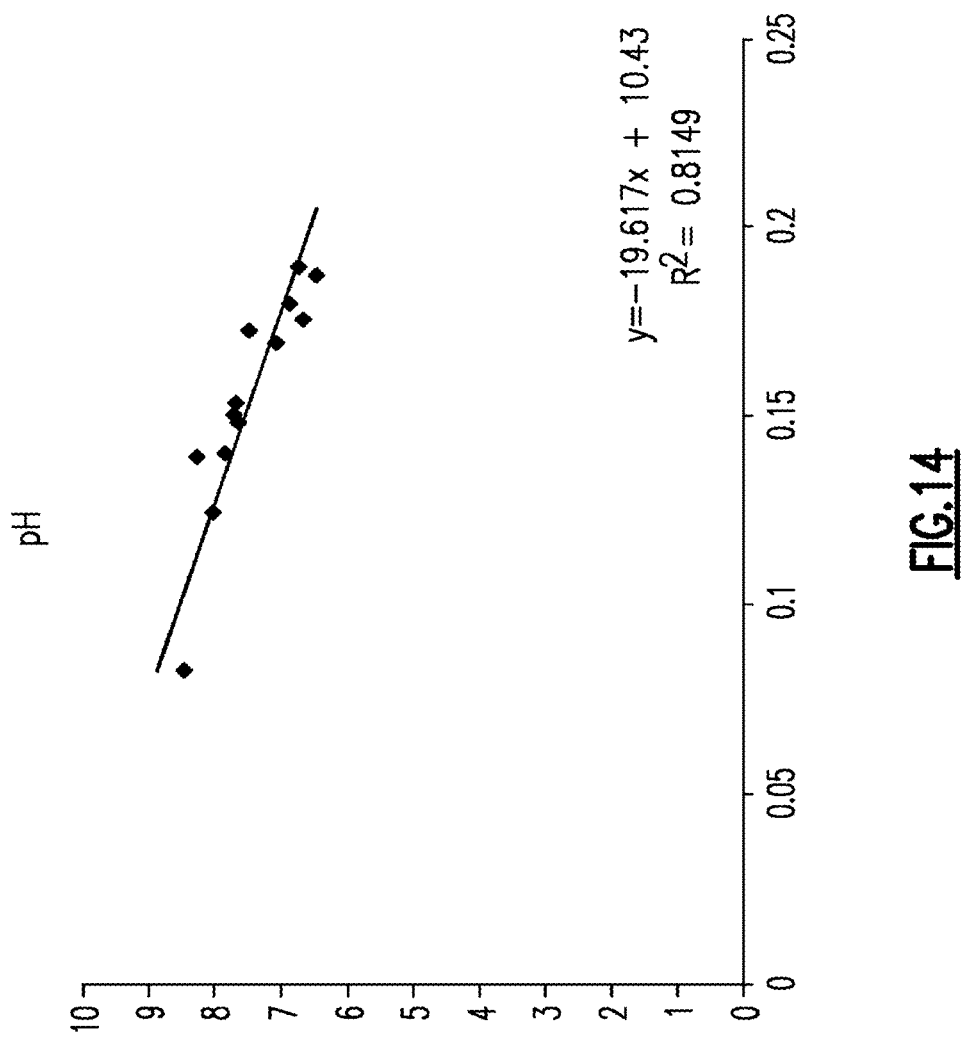
FIG. 14 shows pH vs $\Delta V_{WE-RE}$ for a low chloride result.

Specifically, FIG. 13 shows the LOAC sensor pH responses following a change in ORP caused by adding DCCy, sodium chloride, sodium bisulfate, sodium bicarbonate to the spa chemistry—displayed along with calibrated reference pH measurement. Chloride high concentration, i.e. NaCl, is more than 1000 ppm. FIG. 14 shows the LOAC sensor pH responses following a change in ORP caused by adding DCCy, sodium bisulfate, sodium bicarbonate to the spa chemistry—displayed along with calibrated reference pH measurement. Chloride low concentration, i.e. NaCl, is less than 200 ppm.

Several examples of managing this multi-functional water quality sensor are discussed below. All examples are based on a sensor as outlined in FIGS. 1 through 7. Examples 1 through 6 describe sensing modes. Examples 7-12 describe additional combination modes, and example 13 describes hypothetical configurations and modes.

Example 1

Apply a current of 0.5 mA to the temperature circuit, i.e. pad segments 12 and 15 of FIG. 1, with a variable temperature dependent resistance of approximately 600 Ohm, and documenting the voltage drop V over the resistor, pad segments 3 and 4 of FIG. 1, and feed the voltage into an algorithm:

$$T_{(C)} = mV + b$$

where V is the voltage drop over resistor and m and b are empirically determined constants for slope and zero intercept.

This example is producing a chip temperature as influenced by media it is exposed to. The sensor output is fast responding to temperature changes within time frame of milliseconds as illustrated by temperature decay pattern resulting from a heat pulse of 35 mW×0.2 sec imposed by heater circuit over pad segment 1 and 6 of FIG. 1. FIG. 8 shows the time resolved temperature profile following repeated heat pulses.

Example 2

Repeated application of heat pulses, as described in example 1, creates a chip temperature profile with peak and base temperatures. As an example—the peak temperature has successfully been inversely related to flow velocity via the algorithm:

$$F_{(T)} = a\left(1 + \left|\frac{\Delta T_{base}}{\Delta t}\right|\right)^l \cdot \left(1 + \frac{\Delta T_{cal}}{T_{cal}}\right)^m \cdot (\Delta T_{peak})^n + b$$

where a,b,l,m,n and $T_{cal}$ are material and sensor geometry dependent constants and $\Delta T/\Delta t$, $\Delta T_{cal}$, $\Delta T_{base}$ and $\Delta T_{peak}$ are variables derived from documentation of sensor temperature (T) over time (t). The algorithm has five elements:

(1) $n^{th}$ power element is the pulse height that correlates to flow,
(2) the $m^{th}$ power element is a temperature calibration that corrects for change in pulse power with temperature, necessitated by convenience of using constant potential excitation rather than constant power excitation,
(3) the $l^{th}$ power element corrects the peak height during base temperature changes,
(4) the a element is a velocity—cross section area adjustment, and
(5) the b element is a zero point adjustment.

This algorithm correlates the flow with the temperature increase as documented by sensor induced by a power load to the heater circuit located close to the sensor. The RTD sensor response to the change in flow is shown in FIG. 5. Sensors documenting flow through cooling rate are generally known as anemometers. As such, the inventive concept could be referred to as a pulse anemometer.

Examples 3-6

A spa bath chemistry was created using city water and additions of dichlorocyanuric acid, DCCy, to adjust chlorination level, additions of sodium bisulfate to decrease pH, sodium bicarbonate to increase pH and sodium chloride to increase conductivity without adjusting pH. A number of bath chemistries were created while documenting conductivity, ORP and pH with LOAC sensor and calibrated independent sensors. The flow velocity over the sensor during conductivity, ORP and pH documentation was in range of 1 m/sec.

Example 3

Application of AC potential to pad segments 7 and 8 of FIG. 1 produces a current response that is a variable of the conducting media separating the electrodes. FIG. 11 shows time resolved result of such a documentation using 6.2 kHz, +−0.25V square wave. Documentation of voltage drop over a known resistor produces a conductivity of the media in its simpler form via the algorithm for the conductivity of the media $\square_s$:

$$\sigma_s = a \cdot \frac{V_{re}}{R_{re}(V_{tot} - V_{re})_S}$$

where a is material constant, $V_{re}$ is the voltage drop over the resistor $R_{re}$, and $V_{tot}$ the applied voltage amplitude. Elaboration on the algorithm can be done to take into account absolute temperature and resistance of the leads.

Example 4

Application of a DC potential signal over pad segments 9 and 11, $V_{WE-CE}$, induces a potential difference between pad segments 10 and 11, $V_{WE-RE}$. $V_{ORP}$ can be correlated to $V_{EW-ER}$ via the linear algorithm:

$$V_{ORP} = aV_{we-re} + b$$

where a and b are empirically determined constants. Using a=−1.314, b=1.7519, for example, a correlation between the LOAC independently determined ORP was created as depicted in FIG. 11. The ORP vs $V_{EW-ER}$ is geometry dependent—the example is created from geometry of FIG. 1 in galvanostatic controlled mode using 600 nA and document $V_{EW-ER}$ as average polarization in 10-12 seconds interval. Similar results are found in potentiostatic mode using $V_{WE-CE}$ polarizations between 0.8 V and 1.4 V.

Example 5

Application of two DC potential signals over pad segments 9 and 11, $V_{WE-CE}$, induces two potential differences between pad segments 10 and 11, $V_{WE-RE}$ pH can be correlated to $\square V_{WE-RE}$ via the linear algorithm:

$$pH = a\Delta V_{(we-re)21} + b$$

where the two polarizations are indexed 2 and 1. The pH vs $\square V_{WE-RE}$ is geometry and chemistry dependent—the example is created from geometry of FIG. 1 in galvanostatic controlled mode using 600 nA and document $V_{we-re}$ as average polarization in 10-12 seconds interval. The chemistry was rich in chloride and the correlation is shown in FIG. 13. Similar results are found in potentiostatic mode using $V_{WE-CE}$ polarizations between 0.8 V and 1.4 V.

Example 6

Application of a two DC potential signals over pad segments 9 and 11, $V_{WE-CE}$, induces two potential differences between pad 10 and 11, $V_{WE-RE}$. pH can be correlated to $\square V_{WE-RE}$ via the linear algorithm:

$$pH = a\Delta V_{(we-re)21} + b$$

where the two polarizations are indexed 2 and 1. The pH vs $\square V_{WE-RE}$ is geometry and chemistry dependent—the example is created from geometry of FIG. 1 in galvanostatic controlled mode using 600 nA and document $V_{EW-ER}$ as average polarization in 10-12 seconds interval. The water was in this series of experiments chloride arm i.e. sodium chloride not added to spa chemistry.

Changing the water chemistry to be chloride low changes the pH dependence. Following correlation was found as shown in FIG. 14. Similar results are found in potentiostatic mode using $V_{WE-CE}$ polarizations between 0.8V and 1.4V.

Examples 7-10

Combination of sensing modes in several cases increase the information value of the individual sensing modes.

Example 7

Examples 1 and 2 described temperature and flow documentation individually by the LOAC. However the pulse approach of Example 2 allows us simultaneously to document temperature and flow. Base temperatures are separating the pulse induced peak temperatures. The base temperatures are directly related to the media temperature given appropriate spacing of pulses. In the example, the flow rate can be resolved to sub-second basis. One of the inventive features is the use of this pulsed power which allows the use of the LOAC RTD to document both flow and temperature without need for additional RTD circuitry to document a reference temperature against which peak temperature otherwise would have to be documented.

Example 8

Examples 4, 5 and 6 show one or more polarizations as the basis for ORP and pH documentation. One would adopt one of the polarizations used for documenting ORP as one of two polarizations used for pH documentation.

Example 9

There are two special cases for evaluation of pH response of the LOAC. Combining the conductivity measure with the choice of pH algorithm allows, for example, to base the most appropriate algorithm on conductivity and, if available, set-up and maintenance history.

Example 10

Total dissolved salt, TDS, can be extrapolated from conductivity measures, see Example 3. In this example, First, conductivity corrected for temperature is determined.

$$\sigma_{s(T)} \sigma_{s(T=20)}(1 + 0.02\Delta T)$$

Then corrected for specific ionic conductivity assuming the conductivity is based on i.e. sodium chloride:

$$TDS = 2.2 \cdot \sigma_{s(T)}$$

Examples 11-12

Interference between measurement modes can be a practical issue overcome conveniently by adopting management practices.

Example 11

Conductivity, pH and ORP electrodes are in combination representing sources of cross over noise making it cumbersome to document conductivity and ORP and conductivity and pH simultaneously. Conductivity, pH and ORP in general are used as basis for maintenance decisions and rapid changes in conductivity, pH and ORP are rare beyond immediately following chemistry maintenance events. Separating in time on one side conductivity and on the other side pH and ORP documentation does therefore not represent a reduction in information retrieved from the LOAC sensor.

Example 12

Example 4, 5 and 6 provided conductivity, ORP and pH information using electrodes 17,18,19,20 and 21. As an example we could use any two electrode combination: 17-18, 17-19, 17-20 . . . but more interesting 19-21 to document conductivity and if adopted eliminating need for electrode 17-18. The bottom line is that in principal, any 2 electrode combination can be used for conductivity documentation and any 3 electrode combination can be used for ORP and pH documentation. We have found that a preferred three electrode combination represented by 19,20 and 21 is optimal for pH ORP in which case electrodes 19 and 21 would be used for conductivity. We have found that a preferred five electrode combination represented by 19, 20 and 21 for pH ORP and 17-18 for conductivity are optimal.

Hypothetical Example 13

Several additional features can be imagined for the three electrode combination represented by electrode 19, 20 and 21 of FIG. 1.

Example 13

Focusing on the reference electrode RE. The reference electrode is of platinum creating general unbiased sensitivity to redox pairs present in solution. Changing electrode material or surface coating to ligand types or covering the electrode with an ion or dissolved gas selective membrane represent an avenue to tailor LOAC sensor to specific sensitivity. For example bonding proteins like immunoglobuline or EDTA will create specific sensitivity to antibodies or calcium respectively while coverage of reference electrode with Nafion or PVC will create selectivity for protons and oxygen/chlorine/ozone respectively. The sensitized reference electrode will create unique polarization relative to Vwe-ce polarization similarly as described for ORP and pH relations in examples 4, 5 and 6.

The above examples give a picture of the scope of the invention but should not be considered limiting for the applications possible.

The subject invention provides a multi-functional sensor that determines both temperature and flow using the same sensor circuit by using a heat pulse technique. The sensor also determines pH, ORP and chlorine levels using a single dedicated three electrode sensor operated in a dynamic mode. Additionally, sequential sensing operation is provided to reduce sensing interference during the various sensing operations.

Thus, a multi-functional sensor is provided for optional sensing of temperature, flow, conductivity, ORP and pH that is comprised of an electrically non-conductive substrate covered with electrically conductive traces patterned out over three regions defined as a proximal region, intermediary region, and distal region. The proximal region is exposed to the media to be sensed and holds at least three conductive traces serving as electrodes for optional conductivity, ORP and pH sensing. The intermediary region is insulated from the media to be sensed and holds at least two conductive traces serving as electrical circuits for optional temperature and flow sensing of the media. The distal region is also insulated from the media and holds conductive traces connected to the proximal electrode traces and intermediary circuit traces. The traces on the distal region terminate in pads that serve as an interface for external connection to sensor.

As discussed above, the three conductive traces that serve as electrodes comprise three concentric circles that are interrupted on their circumferences to connect to the traces. The radially outer electrode is the counter electrode, the radially inner electrode is the working electrode, and the radially intermediary electrode between the inner and outer electrodes is the reference electrode.

A pulse anemometer mode of operating the multi-functional sensor includes the following steps. A temperature profile is created that is comprised of peak and valley temperatures of the substrate exposed to a media via heat pulses defined by a power, a power duration, and a power off duration. The peak and valley temperatures of the substrate are documented as a measure of the flow and velocity of the media. In one example, the power duration is between 0.01 seconds and 0.5 seconds, and the power off duration is at least 0.3 seconds.

A dynamic mode of operating a three electrode setup for ORP documentation includes the following steps. A constant potential or a constant current is established between the working electrode and the counter electrode. The potential between the working electrode and the reference electrode is documented as a measure of the ORP. In one example, the constant potential between the working electrode and counter electrode should be chosen between 0.8 V and 2.0 V, or between −0.8V and −2.0V. In one example, the first constant current between working electrode and counter electrode should be chosen between 100 and 600 nA, or between −100 and −600 nA.

A dynamic mode of operating a three electrode setup for pH documentation includes the following steps. A first constant potential or a first constant current is established between the working electrode and the counter electrode. The potential between the working electrode and the reference electrode is defined as a first documented potential. A second constant potential or a second constant current is established between the working electrode and the counter electrode. The potential between the working electrode and the reference electrode for this is then defined as a second documented potential. Finally, the difference between the first and second documented potentials between the working and reference electrodes is established as a measure of the pH. In one example, the first constant potential between the working electrode and counter electrode should be chosen between 0.8 V and 2.0 V, or between −0.8 V and −2.0 V. In one example, the second constant potential between the working electrode and counter electrode should be chosen between 0.8 V and 2.0 V, or between −0.8 V and −2.0 V such that the difference between the two potentials is at least 0.2 V but does not exceed 0.6 V. In one example, the first constant current between the working electrode and counter electrode should be chosen between 100 and 600 nA, or between −100 and −600 nA. In one example, the second constant current between the working electrode and counter electrode should be chosen between 100 and 600 nA, or between −100 and −600 nA, such that the difference between the two currents is at least 100 nA but does not exceed 400 nA.

Further examples of materials or processing of the multi-functional sensor include the following. In one example, the conductive trace that forms the reference electrode is optionally covered by an ion selective membrane, a gas permeable membrane, or a carbon coating. In one example, the ion selective coating is nafion. In one example, the gas permeable coating is PVC. In one example, the carbon coating is a DLC or a ta:C coating optionally modified with ligands. In one example, the ligands can comprise ethylenediamminetetraacetate (EDTA).

The subject sensor assembly, in one example, comprises a silicon chip with electrodes, circuitries, leads and pads made of platinum mounted on and wire bonded to a printed circuit board as described above. The sensor assembly is inserted in a housing and potted with a resin such that the chip electrodes are exposed to the exterior while the circuitries, leads, pads are insulated from the exterior by resin and the housing. In one example, the housing is equipped with features for bayonet fitting to a T connection and the PCB is equipped with a jack for external connection (FIGS. 6-7). In one example, the housing is molded in glass filled polypropylene and the silicon material for the chip substrate is a nonconductive grade having a thickness 0.55 mm or less. In one example, the silicon chip with the circuitries has been annealed at 375 degrees C. for two hours in an inert atmosphere. In one example, the platinum material has been deposited in a sputtering process starting with titanium in a thickness of 100 nm range overcoated with platinum in a 1000 nm thickness range.

Optionally, the circuitries and leads are overcoated with a coating chosen from materials such as, PtO, SiNx, SiNxOy, SiNixOyCz, for example, in a thickness of more than about 1000 nm.

The individual sensing function and any combination of the multiple principal sensor functions and derivatives of these functions such as equivalent chlorine sensing, equivalent ozone sensing, equivalent Total Dissolved Salt, TDS can also be determined with the subject sensor. Further, a sensor noise reduction is provided by the use of a grounded inlet-outlet grid in a T-connection. The T-connection thus includes a noise reduction feature in the form of grounded metal mesh material, for example, that "filters" the flow of some corrosion resistant materials, such as NiSn cladded copper, for example. The mesh has a mesh size providing minimal pressure drop, such as 0.2 mm wire gauge woven in mesh size of 1 mm×1 mm for example, and connected to ground. In one example, there are meshes at the entrance and exit of the T-connection housing the sensing volume.

The purpose of this invention is to provide an inexpensive unified sensor package with ability to output measures of temperature, flow, conductivity, ORP and pH in continuous operation with an accuracy sufficient to provide feedback for safe spa operation. While the primary aim for the invention is use in a spa bath the size, design, cost and concepts making up the invention lend itself equally well to a broad range of applications calling for individual or combined in situ documentation of temperature, flow, conductivity, ORP and pH and the derivatives thereof such as equivalent chlorine, oxygen or ozone concentration as well as Total Dissolved Salt (TDS). Further, specifics of the configuration lend itself well to continued development accomplished by mode of operation sophistication as well as electrode modifications.

The subject invention can be used for water quality determinations in a spa application as well as in pool water, in city water quality characterization for commercial and domestic use, washing machines, dish washers, coffee brewers, soft drink dispensers, drinking fountains, faucets, thermostats for faucets, ice makers, water dispensers, fridge water dispensers, conditioned water dispensers such as chlorinated water dispensers, ozonated water dispensers, sterilized water dispensers, in filter applications, reverse osmosis filter applications, in electrolyzer applications, and in fuel cell applications, for example. It also be used in medical applications such as in situ flow and blood characterization applications, in renal and urine characterization applications. The claimed sensor platform approach lends itself well to customization in mass production at a low price point due to common chip design for manufacture of sensors for an array of application.

The preceding description is exemplary rather than limiting in nature. Variations and modifications to the disclosed examples may become apparent to those skilled in the art that do not necessarily depart from the essence of this disclosure. The scope of legal protection given to this disclosure can only be determined by studying the following claims.

Although a combination of features is shown in the illustrated examples, not all of them need to be combined to realize the benefits of various embodiments of this disclosure. In other words, a system designed according to an embodiment of this disclosure will not necessarily include all of the features shown in any one of the Figures or all of the portions schematically shown in the Figures. Moreover, selected features of one example embodiment may be combined with selected features of other example embodiments.

The invention claimed is:

1. A sensor assembly for water, the sensor assembly comprising:
    an electrically non-conductive substrate; and
    electrically conductive traces carried by the electrically non-conductive substrate, the electrically conductive traces comprising electrical circuits to sense a temperature of the water and a flow rate of the water,
    wherein the electrical circuits comprise:
        a temperature sensor circuit configured to determine the temperature of the water; and
        a heater circuit configured to produce a temperature increase,
    wherein a dissipation of the temperature increase is a function of the flow rate of the water passing the sensor assembly such that the dissipation is translated into the flow rate of the water, and
    wherein the electrically conductive traces further comprise three electrodes to sense acidity (pH) of the water.

2. The sensor assembly of claim 1, wherein the electrically conductive traces defining the three electrodes comprise three concentric circles.

3. The sensor assembly of claim 2, wherein the three concentric circles are arranged such that a radially outer electrode is configured as a counter electrode, a radially inner electrode is configured as a working electrode, and a radially intermediary electrode is configured as a reference electrode.

4. A sensor assembly for water, the sensor assembly comprising:
    an electrically non-conductive substrate; and
    electrically conductive traces carried by the electrically non-conductive substrate, the electrically conductive traces comprising electrical circuits to sense a temperature of the water and a flow rate of the water,
    wherein the electrical circuits comprise:
        a temperature sensor circuit configured to determine the temperature of the water; and
        a heater circuit configured to produce a temperature increase,
    wherein a dissipation of the temperature increase is a function of the flow rate of the water passing the sensor assembly such that the dissipation is translated into the flow rate of the water, and
    wherein the electrically conductive traces further comprise three electrodes to sense oxidation reduction potential (ORP) of the water.

5. A sensor assembly for water, the sensor assembly comprising:
    an electrically non-conductive substrate; and
    electrically conductive traces carried by the electrically non-conductive substrate, the electrically conductive traces comprising electrical circuits to sense a temperature of the water and a flow rate of the water,
    wherein the electrical circuits comprise:
        a temperature sensor circuit configured to determine the temperature of the water; and
        a heater circuit configured to produce a temperature increase,
    wherein a dissipation of the temperature increase is a function of the flow rate of the water passing the sensor assembly such that the dissipation is translated into the flow rate of the water, and
    wherein:
        the electrically conductive traces further comprise conductivity electrodes to sense conductivity; and
        the electrically conductive traces further comprise three electrodes to sense acidity (pH) of the water, oxidation reduction potential (ORP) of the water, or both the pH and ORP of the water.

6. A sensor assembly for water, the sensor assembly comprising:
    an electrically non-conductive substrate; and
    electrically conductive traces carried by the electrically non-conductive substrate, the electrically conductive traces comprising electrical circuits to sense a temperature of the water and a flow rate of the water,
    wherein the electrical circuits comprise:
        a temperature sensor circuit configured to determine the temperature of the water; and a heater circuit configured to produce a temperature increase, wherein a dissipation of the temperature increase is a function of the flow rate of the water passing the sensor assembly such that the dissipation is translated into the flow rate of the water, and wherein the electrically conductive traces further comprise three electrodes to sense, by respective modes of operation, conductivity of the water, acidity (pH) of the water, and the oxidation reduction potential (ORP) of the water.

\* \* \* \* \*